United States Patent
Orford et al.

(10) Patent No.: US 10,617,674 B2
(45) Date of Patent: *Apr. 14, 2020

(54) DOSAGE REGIMEN FOR THE TREATMENT OF ACUTE EXACERBATIONS OF INFLAMMATORY CONDITIONS

(71) Applicant: MEREO BIOPHARMA 1 LIMITED, London (GB)

(72) Inventors: Colin Orford, London (GB); Cyril Clarke, London (GB); Colm Farrell, London (GB); Jacqueline Parkin, London (GB); Stefan De Buck, Basel (CH)

(73) Assignee: MEREO BIOPHARMA 1 LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/082,772

(22) PCT Filed: Mar. 8, 2016

(86) PCT No.: PCT/GB2016/050635
§ 371 (c)(1),
(2) Date: Sep. 6, 2018

(87) PCT Pub. No.: WO2017/153701
PCT Pub. Date: Sep. 14, 2017

(65) Prior Publication Data
US 2019/0091203 A1    Mar. 28, 2019

(51) Int. Cl.
*A61K 31/415* (2006.01)
*A61P 11/00* (2006.01)
*A61P 29/00* (2006.01)
*A61K 9/00* (2006.01)

(52) U.S. Cl.
CPC .......... *A61K 31/415* (2013.01); *A61P 11/00* (2018.01); *A61P 29/00* (2018.01); *A61K 9/0053* (2013.01)

(58) Field of Classification Search
USPC ........................................... 514/407
See application file for complete search history.

(56) References Cited

U.S. PATENT DOCUMENTS

| 6,899,099 | B2 | 5/2005 | Andersson et al. |
| 9,339,491 | B2 | 5/2016 | Ford |

| 2005/0049288 | A1* | 3/2005 | Fryszman | C07D 231/38 514/365 |
| 2005/0277602 | A1* | 12/2005 | Grunstein | A61K 31/573 514/35 |
| 2009/0270350 | A1* | 10/2009 | Devadas | C07D 401/12 514/63 |

FOREIGN PATENT DOCUMENTS

| WO |  | 2005/009973 A1 | 2/2005 |
| WO | WO | 2005110452 A2 | 11/2005 |
| WO | WO | 2007096151 A2 | 8/2007 |
| WO |  | 2013/139809 A1 | 9/2013 |

OTHER PUBLICATIONS

De Buck et. al. (CPT Phamacometrics Syst. Pharmacol. (Nov. 2015) 4:691-700 (Year: 2015).*
De Buck et al.,"Population PK-PD Model for Tolerance Evaluation to the p38 MAP Kinase Inhibitor BCT197", CPT Pharmacometrics Syst Pharmacol. Dec. 2015;4(12):691-700. doi: 10.1002/psp4. 12037. Epub Nov. 9, 2015.
Ikeda et al., "Pharmacological treatment in acute exacerbations of chronic obstructive pulmonary disease", Drugs Aging. Feb. 1998;12(2):129-37. Review.
Norman et al., "Investigational p38 inhibitors for the treatment of chronic obstructive pulmonary disease", Expert Opin Investig Drugs. Mar. 2015;24(3):383-92. doi: 10.1517/13543784.2015.1006358. Epub Jan. 20, 2015. Review.
International Search Report and Written Opinion issued in PCT/GB2016/050635 dated Mar. 3, 2017 (15 pages).
D. Hammaker and G. S. Firestein, ""Go upstream, young man": lessons learned from the p38 saga" Ann Rheum Dis. Jan. 2010; 69 (Suppl 1): i77-i82. doi:10.1136/ard.2009.119479. (14 pages).
Office Action dated Apr. 3, 2019 in U.S. Appl. No. 16/082,765 (11 pages).
International Preliminary Report on Patentability issued in PCT/GB2016/050636 dated Sep. 11, 2018 (8 pages).
Trial record for NCT01332097, Safety & Efficacy of BCT197A2201 in Chronic Obstructive Pulmonary Disease (COPD) Patients Presenting with an Exacerbation, last update posted Feb. 20, 2014, US National Library of Medicine, retrieved from https://ClinicalTrials.gov on Dec. 19, 2019 (6 pages).

* cited by examiner

*Primary Examiner* — Marcos L Sznaidman
(74) *Attorney, Agent, or Firm* — Wolff IP, A Prof. Corp.; Jessica Wolff

(57) ABSTRACT

This invention relates to a novel dosage regimen for administration of 3-[5-amino-4-(3-cyanobenzoyl)-pyrazol-1-yl]-N-cyclopropyl-4-methylbenzamide or a pharmaceutically acceptable derivative thereof, namely in the treatment of acute exacerbations of inflammatory conditions.

16 Claims, 4 Drawing Sheets

DOSAGE REGIMEN FOR THE TREATMENT OF ACUTE EXACERBATIONS OF INFLAMMATORY CONDITIONS

CROSS-REFERENCE TO RELATED APPLICATIONS

The present invention is filed under 35 U.S.C. § 371 as the U.S. national phase of International Patent Application No. PCT/GB2016/050635, filed Mar. 8, 2016, which designated the United States, and which is hereby incorporated in its entirety including all tables, figures, and claims.

FIELD OF THE INVENTION

This invention relates to a novel dosage regimen for administration of 3-[5-amino-4-(3-cyanobenzoyl)-pyrazol-1-yl]-N-cyclopropyl-4-methylbenzamide or a pharmaceutically acceptable derivative thereof, namely in the treatment of acute exacerbations of inflammatory conditions.

BACKGROUND OF THE INVENTION

A large number of cytokines participate in the inflammatory response, including interleukin-1 (IL-1), IL6, IL-8 and TNF-α. Overproduction of cytokines such as IL-1 and TNF-α are implicated in a wide variety of diseases, including inflammatory bowel disease, asthma, rheumatoid arthritis, psoriasis, vasculitis, multiple sclerosis, endotoxin shock, osteoporosis, Alzheimer's disease, and congestive heart failure, among others.

Evidence in human patients indicates that protein antagonists of cytokines are effective in treating chronic inflammatory diseases. International patent application WO2005/009973 discloses various pyrazole- and imidazole-based compounds or pharmaceutically acceptable derivatives thereof that have cytokine inhibitory activity. It discloses such compounds can be used to treat conditions associated with p38 kinases, especially p38a and β kinases, including asthma, allergies and adult respiratory distress syndrome. WO2005/009973 discloses 3-[5-amino-4-(3-cyanobenzoyl)-pyrazol-1-yl]-N-cyclopropyl-4-methylbenzamide as one such novel pyrazole-based p38 kinase inhibitor and describes processes for its preparation. 3-[5-Amino-4-(3-cyanobenzoyl)-pyrazol-1-yl]-N-cyclopropyl-4-methylbenzamide has the following chemical structure:

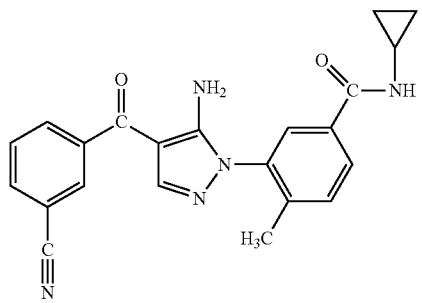 [SMILES: Cc1ccc(C(=O)NC2CC2)cc1-n1ncc(C(=O)c2cccc(C#N)c2)c1N]

Acute exacerbations of inflammatory diseases are associated with increased mortality and impaired quality of life.

It has surprisingly been found that the dosage regimens of the present invention are particularly effective for treating acute exacerbations of inflammatory diseases.

SUMMARY OF THE INVENTION

In a first aspect, the invention provides a pharmaceutical composition for the treatment of acute exacerbations of an inflammatory disease in a human patient, comprising administering to the patient three to five separate therapeutically effective doses of 3-[5-amino-4-(3-cyanobenzoyl)-pyrazol-1-yl]-N-cyclopropyl-4-methylbenzamide or a pharmaceutically acceptable derivative thereof over a minimum period of five days and a maximum period of ten days, with at least one day between every dose. The doses are administered over a period of not longer than 10 consecutive days.

In a second aspect, the invention provides a pharmaceutical composition for the alleviation of a symptom of acute exacerbations of an inflammatory disease in a human patient, comprising administering to the patient three to five separate therapeutically effective doses of 3-[5-amino-4-(3-cyanobenzoyl)-pyrazol-1-yl]-N-cyclopropyl-4-methylbenzamide or a pharmaceutically acceptable derivative thereof over a minimum period of five days and a maximum period of ten days, with at least one day between every dose.

In a third aspect, the invention provides a pharmaceutical composition for increasing the tolerability of 3-[5-amino-4-(3-cyanobenzoyl)-pyrazol-1-yl]-N-cyclopropyl-4-methylbenzamide or a pharmaceutically acceptable derivative thereof in a human patient, comprising administering to the patient three to five separate therapeutically effective doses of 3-[5-amino-4-(3-cyanobenzoyl)-pyrazol-1-yl]-N-cyclopropyl-4-methylbenzamide or a pharmaceutically acceptable derivative thereof over a minimum period of five days and a maximum period of ten days, with at least one day between every dose.

In a fourth aspect, the invention provides a method for the treatment of acute exacerbations of an inflammatory disease in a human patient suffering from an inflammatory disease comprising administering to the human patient three to five separate therapeutically effective doses of 3-[5-amino-4-(3-cyanobenzoyl)-pyrazol-1-yl]-N-cyclopropyl-4-methylbenzamide or a pharmaceutically acceptable derivative thereof over a minimum period of five days and a maximum period of ten days, with at least one day between every dose.

In a fifth aspect, the invention provides a method of alleviating a symptom of an acute exacerbation of an inflammatory disease in a human patient, comprising administering to the human patient three to five separate therapeutically effective doses of 3-[5-amino-4-(3-cyanobenzoyl)-pyrazol-1-yl]-N-cyclopropyl-4-methylbenzamide or a pharmaceutically acceptable derivative thereof over a minimum period of five days and a maximum period of ten days, with at least one day between every dose.

In a sixth aspect, the invention provides a method of increasing the tolerability of 3-[5-amino-4-(3-cyanobenzoyl)-pyrazol-1-yl]-N-cyclopropyl-4-methylbenzamide or a pharmaceutically acceptable derivative thereof in a human patient suffering from an inflammatory disease, which comprises administering three to five separate doses of a pharmaceutical composition comprising 3-[5-amino-4-(3-cyanobenzoyl)-pyrazol-1-yl]-N-cyclopropyl-4-methylbenzamide or a pharmaceutically acceptable derivative thereof, over a minimum period of five days and a maximum period of ten days, with at least one day between every dose.

In a seventh aspect, the invention also provides a kit comprising three to five separate therapeutically effective doses of 3-[5-amino-4-(3-cyanobenzoyl)-pyrazol-1-yl]-N-cyclopropyl-4-methylbenzamide or a pharmaceutically acceptable derivative thereof; and instructions for treating a human patient suffering from an acute exacerbation of an inflammatory disease, said instructions comprising directions to administering said doses separately over a minimum period of five days and a maximum period of ten days, with at least one day between every dose administration.

In an eighth aspect, the invention also provides a kit comprising three to five separate therapeutically effective doses of 3-[5-amino-4-(3-cyanobenzoyl)-pyrazol-1-yl]-N-cyclopropyl-4-methylbenzamide or a pharmaceutically acceptable derivative thereof; and instructions for treating a human patient suffering from an acute exacerbation of an inflammatory disease, said instructions comprising directions for administering said doses separately over a minimum period of five days and a maximum period of ten days, with at least one day between every dose administration.

In a highly preferred embodiment, any of the methods, compositions or kits disclosed above comprise administering three doses separately over a period of five to seven days, with at least one day between every dose administration. Preferably the dosing is on days 1, 3 and 5.

In another highly preferred embodiment, any of the methods, compositions or kits disclosed above comprise administering four doses separately over a period of seven to ten days, with at least one day between every dose administration. Preferably the dosing is on days 1, 4, 7 and 10.

In another preferred embodiment, any of the methods, compositions or kits disclosed above comprise administering five doses separately over a period of ten days, with at least one day between every dose administration. It is known that with each exacerbation there is an acute inflammatory reaction, which in severe cases leads to tissue destruction and more severe and prolonged inflammation. This can be fatal. It is in these specific patients, wherein administration over a maximum of 10 days may be particularly beneficial, and wherein dosing with a maximum of five doses over a period of 10 days is particularly beneficial. This may also be beneficial in patients that have a co-existing condition (examples being presence of COPD in an acute asthma exacerbation or presence of co-existing infection) that impacts the severity of the acute exacerbation being treated.

In a particularly preferred embodiment, any of the compositions, methods and kits described above are used in the treatment or alleviation of acute exacerbations of asthma. Preferably, when treating asthma, three doses are administered, and the dosing is on days 1, 3 and 5.

DETAILED DESCRIPTION OF THE INVENTION

Patients who have inflammatory diseases may experience an acute exacerbation i.e. a sudden and serious worsening of their condition that requires hospitalisation and medical intervention to return the patient to a stable condition. Physicians typically treat patients experiencing an acute exacerbation with oral steroids (for example prednisone), immunosuppressive medication and/or antibiotics and/or oxygen if the condition affects the respiratory tract, but the clinical benefit, especially for steroids, is marginal. On average a patient will need to spend several days or even weeks in hospital to recover to the previous stable disease state. Sometimes the recovery is not complete. Some acute exacerbations prove fatal.

According to the present invention, preferably there are administrable doses, preferably unit doses, to be administered over a period of 7 to 10 days, and there must be at least one day between each dose administration. The doses are preferably administered over a minimum of 7 days and a maximum of 10 days. Preferably, the dose administration takes place every other day. Preferably, each separate dose has at least a 36 hour period between each administration, preferably at least 42 hours between each administration.

Preferred administration schedules according to the present invention include Day 1, Day 3, Day 7; Day 1, Day 4, Day 6; Day 1, Day 4, Day 7; Day 1, Day 5, Day 7; Day 1, Day 3, Day 5, Day 7; Day 1, Day 3, Day 5, Day 7, Day 9; Day 1, Day 3, Day 6, Day 8; Day 1, Day 3, Day 7, Day 10; Day 1, Day 3, Day 5, Day 7, Day 10; Day 1, Day 4, Day 7, Day 9; Day 1, Day 4, Day 6, Day 8, Day 10; or Day 1, Day 5, Day 7, Day 9.

Figure 1:
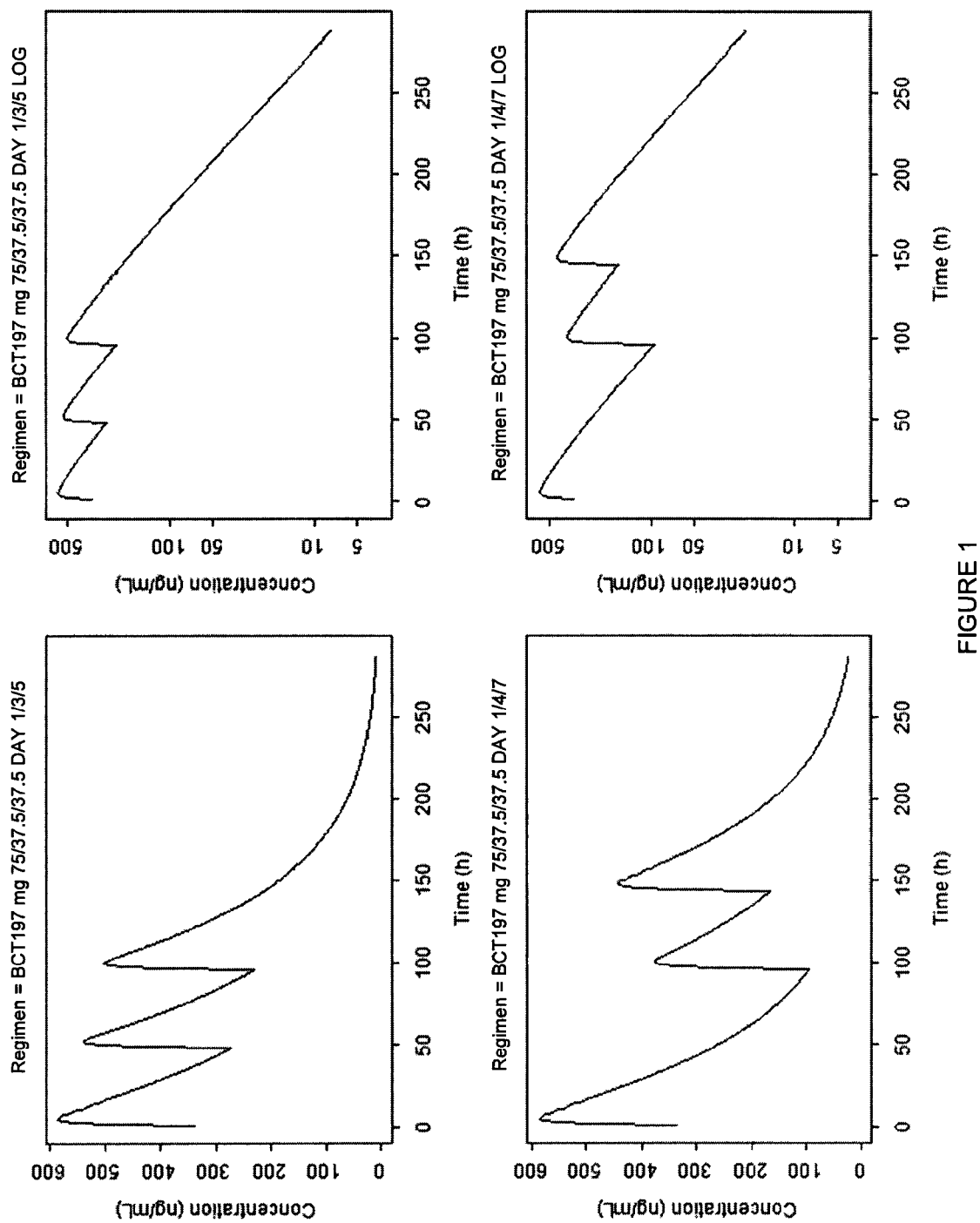
FIG. 1: PK profile for a 75/37.5/37.5 mg dosing regime of 3-[5-amino-4-(3-cyanobenzoyl)-pyrazol-1-yl]-N-cyclopropyl-4-methylbenzamide (referred to as BCT197) at days 1/3/5 (upper left-hand panel) and at days 1/4/7 (bottom left-hand panel). Right-hand panels are log transformed data.
Figure 2:
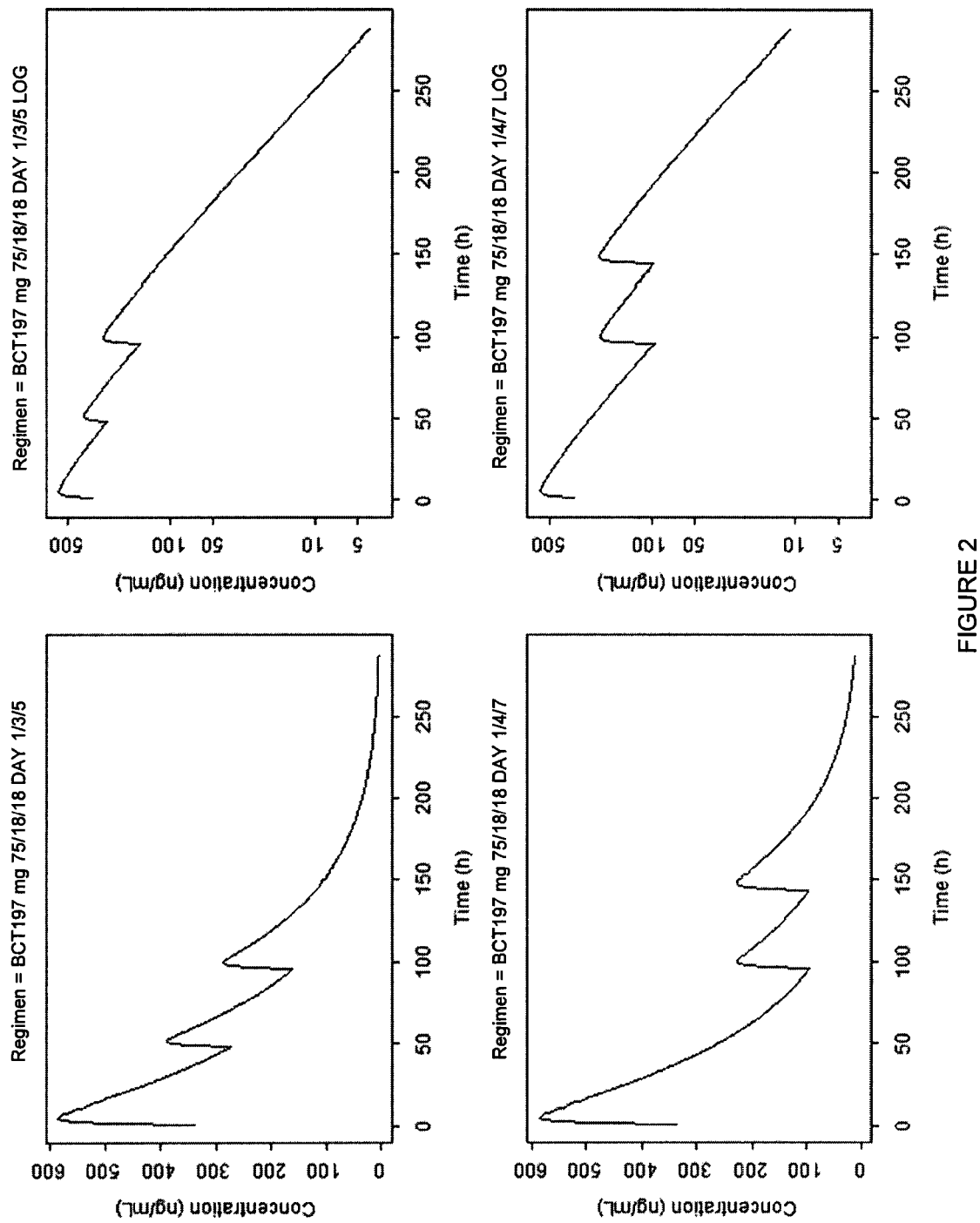
FIG. 2: PK profile for a 75/18/18 mg dosing regime of 3-[5-amino-4-(3-cyanobenzoyl)-pyrazol-1-yl]-N-cyclopropyl-4-methylbenzamide (referred to as BCT197) at days 1/3/5 (upper left-hand panel) and at days 1/4/7 (bottom left-hand panel). Right-hand panels are log transformed data.
Figure 3:
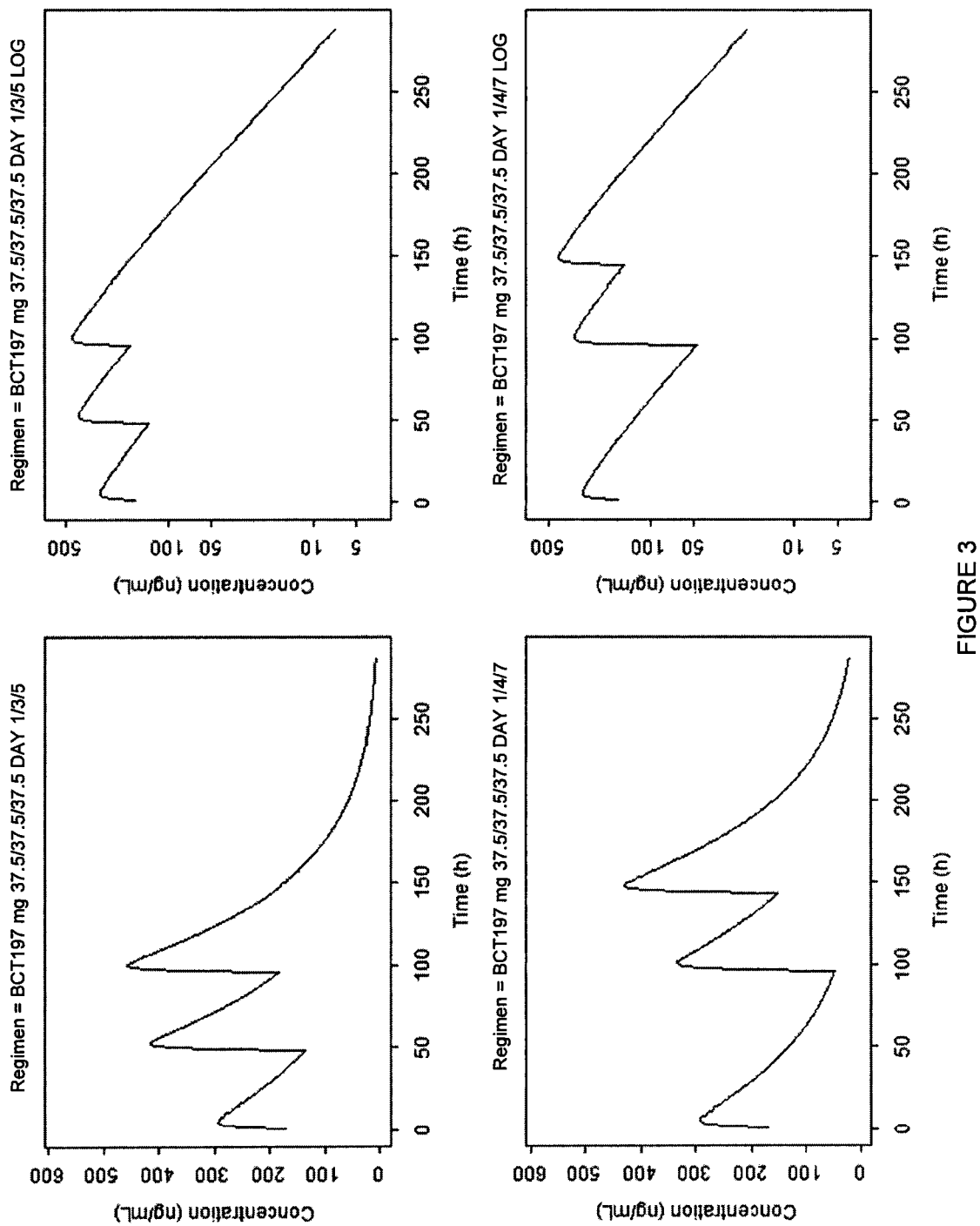
FIG. 3: PK profile for a 37.5/37.5/37.5 mg dosing regime of 3-[5-amino-4-(3-cyanobenzoyl)-pyrazol-1-yl]-N-cyclopropyl-4-methylbenzamide (referred to as BCT197) at days 1/3/5 (upper left-hand panel) and at days 1/4/7 (bottom left-hand panel). Right-hand panels are log transformed data.
Figure 4:
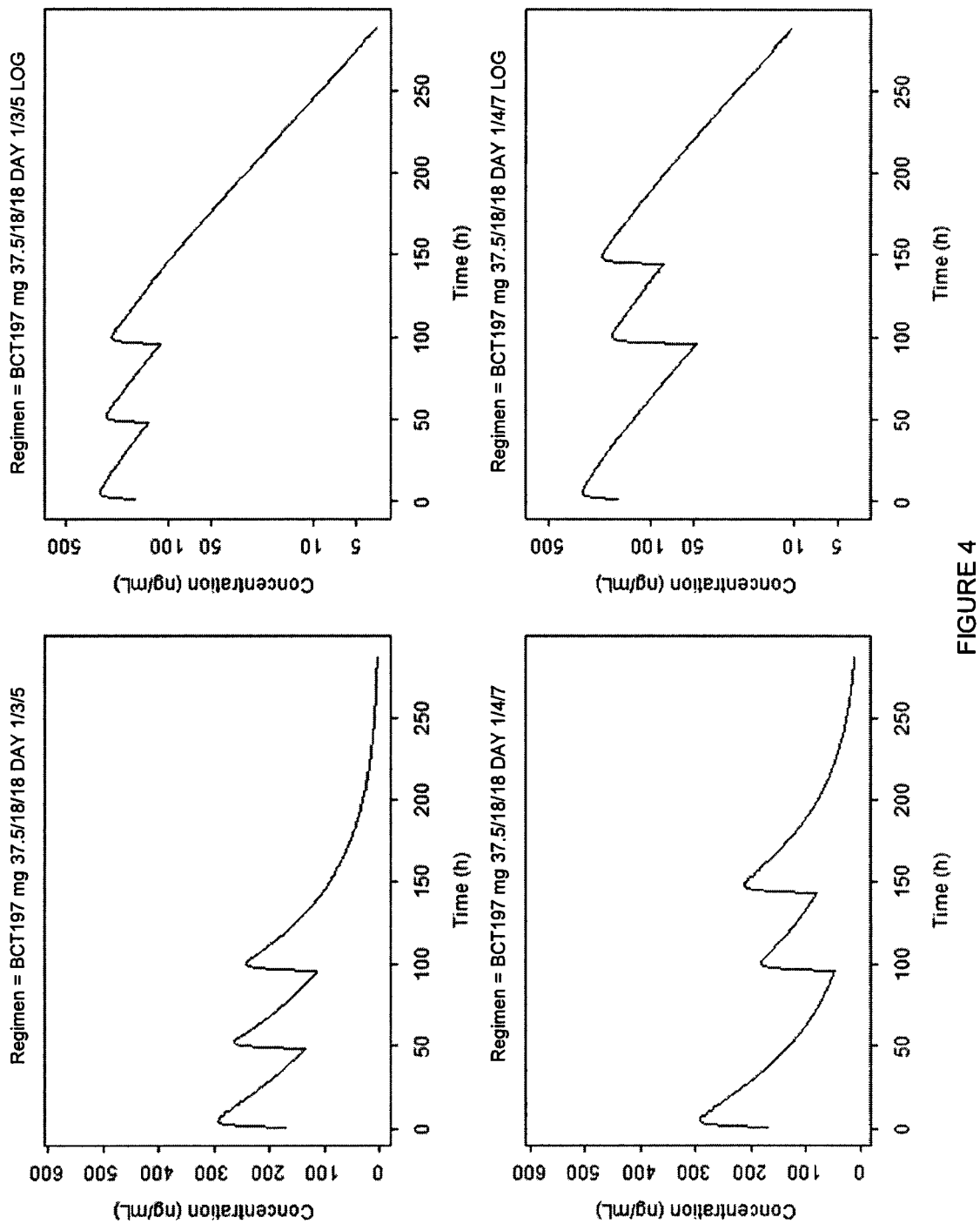
FIG. 4: PK profile for a 37.5/18/18 mg dosing regime of 3-[5-amino-4-(3-cyanobenzoyl)-pyrazol-1-yl]-N-cyclopropyl-4-methylbenzamide (referred to as BCT197) at days 1/3/5 (upper left-hand panel) and at days 1/4/7 (bottom left-hand panel). Right-hand panels are log transformed data.

Most preferably, dosing is at least on days 1, 3 and 5 or at least on days 1, 4 and 7, most preferably at least on days 1, 3 and 5. FIGS. 1 to 8 show the dose profiles for 3-[5-amino-4-(3-cyanobenzoyl)-pyrazol-1-yl]-N-cyclopropyl-4-methylbenzamide given on days 1, 3 and 5 and days 1, 4 and 7 respectively.

Each of the three doses is for parenteral, oral or pulmonary delivery. Preferably oral dosage forms include oral liquids, suspensions, elixirs or solid dosage forms such as tablets capsules and sublingual tablets. Preferably, each of the oral doses is in the same physical form, i.e., solid oral dosage form, liquid oral dosage form, parenteral or DPI. Injection, or parenteral dosing, includes subcutaneous, intramuscular and intravenous injection. It will be understood to the skilled person that in the case of serious acute exacerbations, the patient may be unable to accept solid oral dosage forms such as tablets, capsules, sublingual tablets and the like, and so the first administration may be given by oral solution, oral suspension, parenteral or DPI administration, and subsequent administrations may be given either by the same delivery vehicle or given by alternative delivery vehicle such as tablet or capsules or sublingual tablets once the patient is able to accept these dosage forms. Preferably, each of the doses of the three dose administration regimen is suitable for oral or pulmonary delivery. More preferably, each of the doses of the three dose administration regimen is suitable for oral delivery. Even more preferably, each of the doses is an oral solid dosage form, Most preferably, each of the doses is a capsule or a tablet.

The term liquid oral dosage form is intended to mean administration in the form of a solution or a suspension formulation. Pulmonary delivery is usually via inhalation of a powder or solution. The skilled person understands the processes and excipients that can be used for providing pulmonary delivery. The drug substance may be micronized.

Preferably, the treatment is discontinued after the three doses have been administered to the patient over the 5 to 10 day period. Preferably, there is a gap of at least 2 weeks before a second or further dosage regimen of the present invention is administered, preferably, at least 4 weeks, preferably at least 3 months, most preferably not until a further exacerbation of the inflammatory disease is encountered.

In an embodiment, alleviating a symptom comprises reducing the frequency of exacerbations. The dosage regime according to the present invention has been found to extend the length of time between exacerbations of inflammatory diseases. The dosage regime according to the present invention has been found to be particularly effective at extending the time between acute exacerbations in inflammatory diseases. The inventors have shown that treatment according to the present invention achieves baseline levels of inflammatory markers more quickly and then increases the length of time until the next exacerbation, leading to better health of the patient.

In a particularly preferred embodiment according to any of the numbered aspects of the invention, the amount of the dose of 3-[5-amino-4-(3-cyanobenzoyl)-pyrazol-1-yl]-N-cyclopropyl-4-methylbenzamide or a pharmaceutically acceptable derivative thereof is reduced over the course of at least the initial three separate administrations. This may be referred to as a descending dosage regimen. Thus, in a preferred embodiment, the initial dose of 3-[5-amino-4-(3-cyanobenzoyl)-pyrazol-1-yl]-N-cyclopropyl-4-methylbenzamide or a pharmaceutically acceptable derivative thereof is at least 20% greater than any of the subsequent doses, preferably at least 30% greater, more preferably 40% greater, most preferably between 50% and 100% greater than the subsequent doses. The third or subsequent doses may be a smaller dose than the second dose. Preferably, the second and further doses are about the same weight. Thus, preferably the ratio of the first dose to any of the subsequent (i.e., second, third, fourth or fifth) dose of 3-[5-amino-4-(3-cyanobenzoyl)-pyrazol-1-yl]-N-cyclopropyl-4-methylbenzamide or a pharmaceutically acceptable derivative thereof is in the range of 1:0.8-1:0.2, preferably 1:0.6-1:0.4.

The therapeutically effective oral dose of 3-[5-amino-4-(3-cyanobenzoyl)-pyrazol-1-yl]-N-cyclopropyl-4-methylbenzamide or a pharmaceutically acceptable derivative thereof, when given orally, is preferably in the range of 10 mg-75 mg, preferably 20 mg-75 mg, preferably 35 mg-75 mg, for example about 18, 25, 30, 35, 37.5, 40, 50, 60, 70 or 75 mg.

In the descending dosage regime referred to above, preferably the first oral dose of 3-[5-amino-4-(3-cyanobenzoyl)-pyrazol-1-yl]-N-cyclopropyl-4-methylbenzamide or a pharmaceutically acceptable derivative thereof is in the range of 10 mg-75 mg, preferably 20 mg-80 mg, preferably 35 mg-75 mg. Most preferably the first oral dose is 75 mg.

Preferably, each of the doses is in the same physical form. Preferably, each of the doses is administered via the same route.

In the descending dosage regime referred to above, preferably the second oral dose of 3-[5-amino-4-(3-cyanobenzoyl)-pyrazol-1-yl]-N-cyclopropyl-4-methylbenzamide or a pharmaceutically acceptable derivative thereof is in the range of 5 mg-60 mg, preferably 10 mg-50 mg, preferably 20 mg-40 mg. Most preferably the second oral dose is 40 mg.

In the descending dosage regime referred to above, preferably the third oral dose of 3-[5-amino-4-(3-cyanobenzoyl)-pyrazol-1-yl]-N-cyclopropyl-4-methylbenzamide or a pharmaceutically acceptable derivative thereof is in the range of 5 mg-60 mg, preferably 10 mg-50 mg, preferably 20 mg-40 mg. Most preferably the third oral dose is 40 mg.

In the descending dosage regime referred to above, preferably any dosage administrations after the third dose of 3-[5-amino-4-(3-cyanobenzoyl)-pyrazol-1-yl]-N-cyclopropyl-4-methylbenzamide or a pharmaceutically acceptable derivative thereof is in the range of 5 mg-60 mg, preferably 10 mg-50 mg, preferably 20 mg-40 mg. Most preferably the fourth and/or fifth oral dose is 40 mg.

In the descending dosage regime referred to above, preferably, the first oral dose of 3-[5-amino-4-(3-cyanobenzoyl)-pyrazol-1-yl]-N-cyclopropyl-4-methylbenzamide or a pharmaceutically acceptable derivative thereof is in the range of 40 mg-75 mg, the second dose of 3-[5-amino-4-(3-cyanobenzoyl)-pyrazol-1-yl]-N-cyclopropyl-4-methylbenzamide or a pharmaceutically acceptable derivative thereof is in the range of 20 mg-40 mg, and the third dose of 3-[5-amino-4-(3-cyanobenzoyl)-pyrazol-1-yl]-N-cyclopropyl-4-methylbenzamide or a pharmaceutically acceptable derivative thereof is in the range of 20 mg-40 mg, with the proviso that the first dose is greater than either the second or third dose. Preferably, this embodiment is used to treat acute exacerbations of inflammatory diseases. More preferably, the first oral dose is 50 mg-75 mg, followed by second and third doses at 30-60 mg, most preferably the second and third doses are about 40 mg. Most preferably the second and third doses are the same dose.

When administered at all, the fourth and/or fifth oral dose of 3-[5-amino-4-(3-cyanobenzoyl)-pyrazol-1-yl]-N-cyclopropyl-4-methylbenzamide or a pharmaceutically acceptable derivative thereof, if administered orally is in the range of 5 mg-40 mg, preferably 5 mg-30 mg, more preferably 10 mg-30 mg, most preferably 20 mg. Preferably the fourth and fifth doses are the same.

In one embodiment, the first oral dose of 3-[5-amino-4-(3-cyanobenzoyl)-pyrazol-1-yl]-N-cyclopropyl-4-methylbenzamide or a pharmaceutically acceptable derivative thereof is about 75 mg, the second oral dose of 3-[5-amino-4-(3-cyanobenzoyl)-pyrazol-1-yl]-N-cyclopropyl-4-methylbenzamide or a pharmaceutically acceptable derivative thereof is about 40 mg, and the third oral dose of 3-[5-amino-4-(3-cyanobenzoyl)-pyrazol-1-yl]-N-cyclopropyl-4-methylbenzamide or a pharmaceutically acceptable derivative thereof is about 40 mg. Most preferably, this embodiment is used to treat acute exacerbations of asthma.

The dosage regimen, particularly the descending dosage regimen according to any of the numbered aspects of the present invention, provides a pharmacokinetic (pk) profile for 3-[5-amino-4-(3-cyanobenzoyl)-pyrazol-1-yl]-N-cyclopropyl-4-methylbenzamide where the dose achieves a mean $C_{max}$ of about 1.0 to about 9.0 µM, preferably of about 2.0 to about 6.0 µM. Further; >99% enzyme inhibition is preferably achieved for greater than 3 days following administration of the first dose, preferably greater than 5 days following the first dose.

If administered parenterally, the therapeutically effective dose of 3-[5-amino-4-(3-cyanobenzoyl)-pyrazol-1-yl]-N-cyclopropyl-4-methylbenzamide or a pharmaceutically acceptable derivative thereof, is preferably in the range of 15 mg-60 mg, preferably 18 mg-50 mg, for example about 18, 20, 25, 30, 35, 40. In the descending dosage regime referred to above, preferably the first parenteral dose of 3-[5-amino-4-(3-cyanobenzoyl)-pyrazol-1-yl]-N-cyclopropyl-4-methylbenzamide or a pharmaceutically acceptable derivative thereof, if administered parenterally, is in the range of 30-60 mg, preferably 30 mg-50 mg, preferably 35 mg-45 mg, most preferably 40 mg, Most preferably, this embodiment is used to treat acute exacerbations of asthma.

In the descending dosage regime referred to above, preferably the second parenteral dose of 3-[5-amino-4-(3-cyanobenzoyl)-pyrazol-1-yl]-N-cyclopropyl-4-methylbenzamide or a pharmaceutically acceptable derivative thereof; if administered parenterally is in the range of 5 mg-40 mg, preferably 5 mg-30 mg, more preferably 10 mg-30 mg, most preferably 20 mg. Preferably the third parenteral dose of 3-[5-amino-4-(3-cyanobenzoyl)-pyrazol-1-yl]-N-cyclopropyl-4-methylbenzamide or a pharmaceutically acceptable derivative thereof, if administered parenterally is in the range of 5 mg-40 mg, preferably 5 mg-30 mg, more preferably 10 mg-30 mg, most preferably 20 mg. Preferably the second and third doses are the same. When administered at all, the fourth and/or fifth parenteral dose of 3-[5-amino-4-(3-cyanobenzoyl)-pyrazol-1-yl]-N-cyclopropyl-4-methylbenzamide or a pharmaceutically acceptable derivative thereof; if administered parenterally is in the range of 5 mg-40 mg, preferably 5 mg-30 mg, more preferably 10 mg-30 mg, most preferably 20 mg. Preferably the fourth and fifth doses are the same. Most preferably, this embodiment is used to treat acute exacerbations of asthma.

As explained above, depending on the patient's condition the skilled person understands that the second or third doses may be given by other routes such as oral dosage form or DPI if the patient is able to tolerate such forms. In a preferred embodiment, patients are administered parenteral doses if they are unable to tolerate oral formulations.

The specific disease exacerbations that may be treated according to any of the aspects of the present invention include, without limitation, acute pancreatitis, asthma, cystic fibrosis, inflammatory bowel disease, ulcerative colitis and Crohn's disease. Preferably, the disease is selected from asthma, inflammatory bowel disease and ulcerative colitis, more preferably an exacerbation thereof. Asthma is a particularly preferred disease target.

Preferably, the first parenteral dose of 3-[5-amino-4-(3-cyanobenzoyl)-pyrazol-1-yl]-N-cyclopropyl-4-methylbenzamide or a pharmaceutically acceptable derivative thereof is about 40 mg, the second parenteral dose of 3-[5-amino-4-(3-cyanobenzoyl)-pyrazol-1-yl]-N-cyclopropyl-4-methylbenzamide or a pharmaceutically acceptable derivative thereof is about 20 mg, and the third parenteral dose of 3-[5-amino-4-(3-cyanobenzoyl)-pyrazol-1-yl]-N-cyclopropyl-4-methylbenzamide or a pharmaceutically acceptable derivative thereof is about 20 mg.

According to the kit embodiment of the invention, the individual dosage forms can be contained in one or more packages which are optionally labelled to indicate which order the dosage forms should be taken in. For example, a package or packages may be labelled "Dose 1", "Dose 2", and "Dose 3". Alternatively, the doses may be labelled "Day 1", "Day 4", "Day 7", or the like.

Preferably each dose within the composition, method or kit of the present invention is an immediate release formulation. The composition, method or kit of the present invention may comprise a larger first dose that is an immediate release formulation in order to quickly increase blood levels of 3-[5-amino-4-(3-cyanobenzoyl)-pyrazol-1-yl]-N-cyclopropyl-4-methylbenzamide, or a derivative thereof, followed by subsequent doses that are both lower strength immediate release formulations.

In an additional embodiment, the pharmaceutical composition is in a dry powder for self-administration by the patient. Preferably, this is administered via a dry powder inhaler.

In a further embodiment, the patient has not received 3-[5-amino-4-(3-cyanobenzoyl)-pyrazol-1-yl]-N-cyclopropyl-4-methylbenzamide or a pharmaceutically acceptable derivative thereof therapy prior to initiation of the separate doses.

In an embodiment, the dosage regimen of the present invention may be used alone or may be used in combination with standard of care (SoC) treatment, which typically involves, but is not limited to use of steroids, anti-inflammatories, immunosuppressives, β2 adrenergic agonists and/or muscarinic antagonists. Antibiotics may additionally be administered if the patient has an infection.

In an embodiment, the pharmaceutical composition is in the form of a dry powder formulation. In this embodiment, the doses are preferably administered from a dry powder inhaler.

In an embodiment, the pharmaceutical composition is in the form of an oral solid dosage form, preferably a tablet or a capsule.

In one embodiment, the pharmaceutical composition comprises one or more pharmaceutically acceptable excipients. Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. These pharmaceutical compositions may be manufactured in a manner that is itself known, e.g., by means of conventional mixing, dissolving, granulating, dragee-making, levigating, emulsifying, encapsulating, entrapping or lyophilizing processes. Proper formulation is dependent upon the route of administration chosen.

When the composition of the invention is formulated as solid oral dosage form, it is preferably a capsule or a tablet, preferably a capsule. The following are preferably also contained in the capsule or tablet form of the invention:

Fillers and flow regulating agents, preferably in an amount of 5 to 60% by weight, related to the capsule weight. Fillers that may for example be considered are starches, celluoses, lactose, saccharose, fructose, sorbitol, mannitol, calcium phosphate, calcium carbonate, calcium sulphate, magnesium carbonate or magnesium oxide. 5-50% by weight are preferably used, relative to the capsule or tablet weight.

Flow regulating agents that may for example be considered are microcrystalline cellulose, lactose, polyglycols, starches, celluloses, talcum, talcum siliconisatum, calcium arachinate or calcium stearate, cetyl alcohol, stearyl alcohol, myristyl alcohol, stearic acid, lauric acid. Should the flow regulating agent not also serve as a filler, preferably 0.5-10% by weight are used hereof, relative to the capsule or tablet weight.

Disintegrants: use is for example made of alginates, starches (corn starch), pectins, carboxymethyl celluloses, polyvinylpolypyrrolidone, ultraamylopectin, betonite. Preferably 1-10% by weight are used, relative to the capsule or tablet weight.

Antiadhesion agents: use is for example made of glycols, talcum, talcum siliconisatum, talcum stearinicum, calcium stearate, aluminium stearate, stearic acid. Preferably, 0.1-10% by weight are used, relative to the capsule or tablet weight.

Binding agents: for example gelatin, cellulose ethers, amyloses pectins, cellulose, dextrose, polyglycols, tragacanth. Preferably, use is made of 0.1-80% by weight, relative to the capsule or tablet weight.

Tablets as well as capsules may be provided with a coating in known manner. It is possible to apply water-soluble, swellable, water insoluble or gastric juice resistant coatings which may be applied to the tablets or capsules from aqueous dispersion or solution or also from solution or dispersion in organic solvents such as for example ethanol, isopropanol, acetone, ether, dichloromethane or methanol.

When the composition of the invention is formulated as a dry powder formulation, in one embodiment the composition additionally comprises a force control agent.

A force control agent is an agent which reduces the cohesion between the fine particles within the powder formulation, thereby promoting deagglomeration upon dispensing of the powder from the dry powder inhaler.

Suitable force control agents are disclosed in WO 96/23485 and WO 2005/105043 and they typically consist of physiologically acceptable material, despite the fact that the material may not always reach the lung.

The force control agent may comprise a metal stearate, or a derivative thereof, for example, sodium stearyl fumarate or sodium stearyl lactylate. Advantageously, it comprises a metal stearate. For example, zinc stearate, magnesium stearate, calcium stearate, sodium stearate or lithium stearate. In one particular embodiment which may be mentioned, the additive material comprises or consists of magnesium stearate.

The force control agent may include or consist of one or more surface active materials, in particular materials that are surface active in the solid state, which may be water soluble or water dispersible, for example lecithin, in particular soya lecithin, or substantially water insoluble, for example solid state fatty acids such as oleic acid, lauric acid, palmitic acid, stearic acid, erucic acid, behenic acid, or derivatives (such as esters and salts) thereof such as glyceryl behenate. Specific examples of such materials are phosphatidylcholines, phosphatidylethanolamines, phosphatidylglycerols and other examples of natural and synthetic lung surfactants; lauric acid and its salts, for example, sodium lauryl sulphate, magnesium lauryl sulphate; triglycerides such as Dynsan 118 and Cutina HR; and sugar esters in general. Alternatively, the force control agent may be cholesterol.

Other possible force control agents include sodium benzoate, hydrogenated oils which are solid at room temperature, talc, titanium dioxide, aluminium dioxide, silicon dioxide and starch. Also useful as force control agents are film-forming agents, fatty acids and their derivatives, as well as lipids and lipid-like materials.

When the composition of the invention is formulated as a dry powder formulation, in one embodiment the composition additionally comprises a carrier. In a further embodiment, the carrier comprises lactose, such as lactose monohydrate.

Oral liquid formulations of the invention may be in the form of oral solutions or suspensions. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of 3-[5-amino-4-(3-cyanobenzoyl)-pyrazol-1-yl]-N-cyclopropyl-4-methylbenzamide, and preferably from about 1 to 50% of 3-[5-amino-4-(3-cyanobenzoyl)-pyrazol-1-yl]-N-cyclopropyl-4-methylbenzamide.

When 3-[5-amino-4-(O-cyanobenzoyl)-pyrazol-1-yl]-N-cyclopropyl-4-methylbenzamide is administered by intravenous or subcutaneous injection, 3-[5-amino-4-(3-cyanobenzoyl)-pyrazol-1-yl]-N-cyclopropyl-4-methylbenzamide will be in the form of a parenterally acceptable aqueous solution. The preparation of such parenterally acceptable solutions, having due regard to pH, isotonicity, stability, and the like, is within the skill in the art. A preferred pharmaceutical composition for intravenous or subcutaneous injection should contain, in addition to the 3-[5-amino-4-(3-cyanobenzoyl)-pyrazol-1-yl]-N-cyclopropyl-4-methylbenzamide or a pharmaceutically acceptable derivative thereof, an isotonic vehicle such as sodium chloride Injection, Ringer's Injection, dextrose Injection, dextrose and sodium chloride Injection, Lactated Ringer's Injection, or other vehicle as known in the art. The pharmaceutical composition of the present invention may also contain stabilizers, preservatives, buffers, antioxidants, or other additives known to those of skill in the art. For injection, the agents of the invention may be formulated in aqueous solutions, preferably in physiologically compatible buffers such as Hanks's solution, Ringer's solution, or physiological saline buffer.

For transmucosal administration, penetrants appropriate to the barrier to be permeated are used in the formulation. Such penetrants are generally known in the art.

The formulations of the present invention may include 3-[5-amino-4-(3-cyanobenzoyl)-pyrazol-1-yl]-N-cyclopropyl-4-methylbenzamide or a pharmaceutically acceptable derivative thereof as the only pharmaceutically active agent. Alternatively, the formulations may include one or more further active agents. The additional active agents may include, for example:

1). Steroid drugs (intraveneous and rectally administered (e.g. enemas) as well as oral and inhaled) such as, for example, alcometasone, beclomethasone, beclomethasone dipropionate, betamethasone, budesonide, clobetasol, deflazacort, diflucortolone, desoxymethasone, dexamethasone, fludrocortisone, flunisolide, fluocinolone, fluometholone, fluticasone, fluticasone proprionate, fluticasone furoate, mometasone furoate, hydrocortisone, prednisolone, dexamethasone, triamcinolone, nandrolone decanoate, neomycin sulphate, rimexolone, methylprednisolone and prednisolone;

2). Antibiotic and antibacterial agents such as, for example, metronidazole, sulphadiazine, triclosan, neomycin, amoxicillin, amphotericin, clindamycin, aclarubicin, dactinomycin, nystatin, mupirocin and chlorhexidine;

3). Systemically active drugs such as, for example, isosorbide dinitrate, isosorbide mononitrate, apomorphine and nicotine;

4). Antihistamines such as, for example, azelastine, chlorpheniramine, astemizole, cetitizine, cinnarizine, desloratadine, loratadine, hydroxyzine, diphenhydramine, fexofenadine, ketotifen, promethazine, trimeprazine and terfenadine;

5). Anti-inflammatory agents such as, for example, piroxicam, benzydamine, diclofenac sodium, naproxen, ketoprofen, ibuprofen, aspirin, heparinoid, nedocromil, sodium cromoglycate, fasafungine and iodoxamide, sulfasalazine, mesalamine, 6-mercapto purine, dapsone, hydroxy-chloroquine, cox inhibitors;

6). Antimuscarinic/anticholinergic agents such as, for example, atropine, benzatropine, biperiden, cyclopentolate, oxybutinin, orphenadine hydrochloride, procyclidine, propantheline, propiverine, tiotropium, tropicamide, trospium, ipratropium bromide, GSK573719 and oxitroprium bromide;

7). Bronchodilators, such as salbutamol, fenoterol, formoterol, indacaterol, vilanterol and salmeterol;

8). sympathomimetic drugs, such as adrenaline, noradrenaline, dexamfetamine, dipirefin, dobutamine, dopexamine, phenylephrine, isoprenaline, dopamine, pseudoephedrine, tramazoline and xylometazoline;

9). Opiates, such as for pain management, such as, for example, buprenorphine, dextromoramide, diamorphine, codeine phosphate, dextropropoxyphene, dihydrocodeine, papaveretum, pholcodeine, loperamide, fentanyl, methadone, morphine, oxycodone, phenazocine, pethidine and combinations thereof with an anti-emetic;

10). Analgesics and drugs for treating migraine such as clonidine, codine, coproxamol, dextropropoxypene, ergotamine, sumatriptan, tramadol and non-steroidal anti-inflammatory drugs;

11). Immunosuppressive drugs such as azathioprine, methotrexate, and cyclosporine;

12). Angiotensin converting enzyme inhibitors;

13). Cytotoxics, such as cyclophosphamide and chlorambucil;

14). Biological therapies such as monoclonal antibodies to cytokines such as anti-TNF therapies for example monoclonal antibodies (e.g. infliximab) and fusion antibody fragment e.g. etanercept); Anti-B-cell monoclonal antibodies, such as anti-C©20) and anti-Blyss, Anti-Interleukin 5, Anti-Interleukin 13, Anti-interleukin 1, Anti-IgE antibody;

15) Leukocyte trafficking inhibitors for example monoclonal antibodies to Integring CD11a, IL-12, and IL-23;

16). Kinase inhibitors, including Janus kinase (JAK) inhibitors, and Syphingosine-1-Phosphate (lyase) inhibitors; and 17). Pharmaceutically acceptable salts of any of the foregoing.

Preferably, when 3-[5-amino-4-(3-cyanobenzoyl)-pyrazol-1-yl]-N-cyclopropyl-4-methylbenzamide is coadministered or added to treatments using other active ingredients, such other active ingredients are preferably selected from steroid drugs, antibiotics, immunosuppressive drugs and mixtures thereof.

All stereoisomers of 3-[5-amino-4-(3-cyanobenzoyl)-pyrazol-1-yl]-N-cyclopropyl-4-methylbenzamide are contemplated, either in admixture or in pure or substantially pure form. 3-[5-amino-4-(3-cyanobenzoyl)-pyrazol-1-yl]-N-cyclopropyl-4-methylbenzamide as used herein embraces all the possible stereo isomers and their mixtures. It embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization. 3-[5-amino-4-(3-cyanobenzoyl)-pyrazol-1-yl]-N-cyclopropyl-4-methylbenzamide may also have prodrug forms. Any compound that will be converted in vivo to provide the bioactive agent is a prodrug. Various forms of prodrugs are well known in the art.

Definitions

Unless defined otherwise, all technical and scientific terms used herein have the same meaning as is commonly understood by one of skill in the art to which the invention(s) belong.

Terms used in the specification have the following meanings:

"Acute exacerbations" or as used herein mean a sudden worsening of any of the symptoms of an inflammatory disease, typically involving decreased airflow and increased lung hyperinflation versus the stable disease. Acute exacerbations generally have a substantial negative impact on the well-being of patients and typically require the patient to receive urgent medical treatment in a hospital in an attempt to return the patient to the previously stable disease state.

"Pharmaceutically acceptable derivative" as used herein means a derivative of the therapeutically active compound in question that is suitable for use as an active ingredient of a pharmaceutical product.

Throughout this specification and in the claims that follow, unless the context requires otherwise, the word "comprise", or variations such as "comprises" or "comprising", should be understood to imply the inclusion of a stated integer or step or group of integers or steps but not the exclusion of any other integer or step or group of integers or steps.

As used herein, pharmaceutically acceptable derivatives of 3-[5-amino-4-(3-cyanobenzoyl)-pyrazol-1-yl]-N-cyclopropyl-4-methylbenzamide include salts, esters, enol ethers, enol esters, acetals, ketals, orthoesters, hemiacetals, hemiketals, acids, bases, solvates or hydrates. Such derivatives may be readily prepared by those of skill in this art using known methods for such derivatization.

Pharmaceutically acceptable salts of 3-[5-amino-4-(3-cyanobenzoyl)-pyrazol-1-yl]-N-cyclopropyl-4-methylbenzamide include, but are not limited to, amine salts, such as but not limited to N,N'-dibenzylethylenediamine; chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines; piperazine and tris (hydroxymethyl) aminomethane; alkali metal salts, such as but not limited to lithium, potassium and sodium; alkali earth metal salts; such as but not limited to barium, calcium and magnesium; transition metal salts; such as but not limited to zinc; and other metal salts, such as but not limited to sodium hydrogen phosphate and disodium phosphate; and also including, but not limited to, nitrates, borates, methanesulfonates; benzenesulfonates; toluenesulfonates; salts of mineral acids, such as but not limited to hydrochlorides, hydrobromides, hydroiodides and sulfates; and salts of organic acids; such as but not limited to acetates, trifluoroacetates; oxalates, benzoates, salicylates; maleates, lactates, malates, tartrates, citrates, ascorbates, succinates, butyrates, valerates and fumarates. In addition, zwitterions ("inner salts") may be formed. In certain embodiments, salt forms of the compounds improve the compounds' dissolution rate and oral bioavailability. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups; including, but not limited to; carboxylic acids, phosphoric acids, phosphinic acids, sulfonic acids, sulfinic acids and boronic acids.

Pharmaceutically acceptable solvates and hydrates of 3-[5-amino-4-(3-cyanobenzoyl)-pyrazol-1-yl]-N-cyclopropyl-4-methylbenzamide are complexes of a compound with one or more solvent or water molecules, or 1 to about 100; or 1 to about 10, or one to about 2, 3 or 4, solvent or water molecules.

In particular the term derivatives covers pharmaceutically acceptable salts, solvates and hydrates of 3-[5-amino-4-(3-cyanobenzoyl)-pyrazol-1-yl]-N-cyclopropyl-4-methylbenzamide Additional embodiments and features are set forth in part in the description that follows, and in part will become apparent to those skilled in the art upon examination of the specification or may be learned by the practice of the invention. This invention is further illustrated by the following example which should not be construed as limiting.

Example 1

Patients received one of two oral dosing regimens of 3-[5-amino-4-(3-cyanobenzoyl)-pyrazol-1-yl]-N-cyclopropyl-4-methylbenzamide or matching oral placebo administered according to the dosing schedules shown in Table 1.

TABLE 1

Study Dosing Schedules

|  | Day 1 | Day 3 | Day 5 |
| --- | --- | --- | --- |
| Regimen 1 | 75 mg | 40 mg | 40 mg |
| Regimen 2 | 40 mg | 20 mg | 20 mg |
| Regimen 3 | Placebo | Placebo | Placebo |

3-[5-amino-4-(3-cyanobenzoyl)-pyrazol-1-yl]-N-cyclopropyl-4-methylbenzamide is intended to be prescribed as a treatment added to standard of care (SoC) of acute exacerbations in asthma and is envisaged to be used for repeated administration. 3-[5-amino-4-(3-cyanobenzoyl)-pyrazol-1-yl]-N-cyclopropyl-4-methylbenzamide is preferably formulated as oral capsules. The two dose regimens used in this study are based on the efficacy, toxicology, pharmacokinetic and safety data. The first regimen used a starting dose of 75 mg on Day 1 then approximately 40 mg on Days 3 and 5. The second regimen uses a dose of approximately 40 mg on Day 1 and approximately 20 mg on Days 3 and 5.

Rationale

This study was conducted in compliance with the protocol and with the International Conference on Harmonisation (ICH) guidelines on Good Clinical Practice (GCP).

This study investigated the efficacy, safety and tolerability of two different dosing regimens of 3-[5-amino-4-(3-cyanobenzoyl)-pyrazol-1-yl]-N-cyclopropyl-4-methyl benzamide added to SoC (systemic corticosteroids and/or antibiotics) versus placebo added to SoC in subjects with severe acute exacerbations of asthma. The proposed doses take into account trough levels based on PK modelling to ensure that the drug rapidly achieves and remains at effective concentrations between doses.

The approach is to provide rapid attenuation of inflammatory responses which occur during a severe acute exacerbation, typically 3 to 5 days, and so multiple dosing will take place to ensure appropriate plasma levels are present to allow effective treatment of an exacerbation.

Overall, a dose-dependent reduction in TNF-α levels has been observed following doses ranging from 0.1 to 75 mg 3-[5-amino-4-(3-cyanobenzoyl)-pyrazol-1-yl]-N-cyclopropyl-4-methylbenzamide, although flattening of this effect to between 45 to 50% of placebo levels occurred between doses of 30 and 75 mg. A number of PK studies have been performed looking at both dosing intervals (Days 1, 3 and 5 (FIGS. 1-4, top panels) versus Days 1, 4 and 7 (FIGS. 1-4 bottom panels)), as well as dose levels (approximately 75/40/40 mg (FIG. 1); approximately 75/20/20 (FIG. 2); approximately 40/40/40 mg (FIG. 3); approximately 40/20/20 mg (FIG. 4), etc.). Based on exposures of the various regimens, there is limited benefit in dosing beyond Day 5 for a typical exacerbation. Hence, the most favoured regimen is one in which doses are administered on days 1, 3 and 5.

However, in order to initiate suppression of the inflammatory response the Day 1 dose in both regimes is higher than the doses on Days 3 and 5. The 'high' dosing regimen (regimen 1) is initiated at 75 mg which is the highest dose which can be safely administered based on toxicology margins whereas the 'low' dose regimen is initiated at a 40 mg dose which approximates to the mid-point in the TNF-α response curve.

The K values for p38a and p38l3 are 49 and 72 nM, respectively, with $IC_{50}$ values of 37 nM and 106 nM, respectively. Dosing at Day 1, 3 and 5, maintains drug levels above 220 ng/mL out to approximately 140 to 150 hours. This achieves a plasma concentration of 5.7 μM.

3-[5-amino-4-(3-cyanobenzoyl)-pyrazol-1-yl]-N-cyclopropyl-4-methylbenzamide has a very low first pass metabolism pre-clinically with the oral bioavailability estimated at 93% in the rat, 87% in the dog and 90% in the monkey. The data show that it is only weakly protein bound with free fraction in man (human plasma samples) ranging from 13 to 25%.

The concentration based on free fraction is at or above 740 nM for the duration of the dosing interval. $C_{max}$ is approximately 2 μM based on the first dose. Estimated drug levels are approximately 7 to 10 times higher in concentration than the $K_i$ and $IC_{50}$ values and therefore >99% enzyme inhibition occurs for 6 days. Assuming a PK variability of 50%, drug levels are 3 to 5 times above the $K_i$ and so would produce high levels of inhibition, potentially in the range of 90 to 99%.

Example 2

Methods

Study population Clinical study CBCT197A2101 was approved by the Ethics Committees of participating centers and conducted in accordance with Good Clinical Practice guidelines and the Declaration of Helsinki. All subjects gave written informed consent before participation. Healthy male and female subjects of non-childbearing potential aged 18-50 years with a body mass index 18-30 kg/m² and body weight >50 kg were eligible to enroll. Subjects were non-smokers in good health as determined by past medical history, physical examination, vital signs, electrocardiogram, and laboratory tests having no significance at screening. Key exclusion criteria included history of significant medical or surgical disease; significant illness within 14 days prior to initial dosing; known history of cardiovascular disease or ECG abnormality; positive urine drug screen; history of any clinically important drug allergy; or use of any investigational drug within 4 weeks prior to initial dosing. Use of any prescription, over-the-counter drugs or herbal medications, as well as consumption of grapefruit was not permitted from 14 days prior to dosing until 7 days following the last dose.

Study Protocol

Part 1 of study CBCT197A2101 was a randomized, double-blind, placebo-controlled, ascending single-dose study to evaluate safety, tolerability, PK and PD of oral 3-[5-amino-4-(3-cyanobenzoyl)-pyrazol-1-yl]-N-cyclopropyl-4-methylbenzamide in healthy subjects. Part 2 was a 14-day, randomized, double-blind, placebo-controlled, ascending multiple dose study evaluating the PK and PD of oral 3-[5-amino-4-(3-cyanobenzoyl)-pyrazol-1-yl]-N-cyclopropyl-4-methylbenzamide. PD effect of 3-[5-amino-4-(3-cyanobenzoyl)-pyrazol-1-yl]-N-cyclopropyl-4-methylbenzamide in Parts 1 and 2 was assessed by measuring TNFa levels in ex vivo LPS-challenged blood samples. Details of the PK and PD sampling regimen, ex vivo LPS challenge, and bioanalysis of 3-[5-amino-4-(3-cyanobenzoyl)-pyrazol-1-yl]-N-cyclopropyl-4-methylbenzamide and TNFa are provided in the Supplementary Methods. Part 3 of the study determined the effect of a single oral administration of 3-[5-amino-4-(3-cyanobenzoyl)-pyrazol-1-yl]-N-cyclopropyl-4-methylbenzamide on serum TNFa levels after in vivo intravenous LPS challenge. Only PK data of this part were used, as it did not measure ex vivo LPS-induced TNFa.

Subjects fasted for 10 hours prior to 3-[5-amino-4-(3-cyanobenzoyl)-pyrazol-1-yl]-N-cyclopropyl-4-methylbenzamide administration and continued to fast for 4 hours post-dosing. No fluid intake apart from the fluid given at the time of drug intake was allowed from 2 hours before until 2 hours after dosing. Drug administrations were oral solutions with doses ranging from 0.1 to 3 mg, and tablets at doses of 5 mg and higher.

Population PK-PD Analysis

A nonlinear mixed-effects model approach with first-order conditional estimation (Lindstrom Bates) in Phoenix 6.4 NLME V1.2 (Pharsight, USA) was used to estimate population parameters and their between-subject variability (BSV). Final model selection was guided by reduction in the objective function value (OFV), precision in parameter estimates, examination of goodness-of-fit, reductions in the magnitude of BSV and residual error, as well as shrinkage in random variability parameters and robust model parameter estimation. Statistical significance between nested models was based on DOFV (3.85), applying the likelihood ratio test. Model stability and performance were assessed by means of a nonparametric bootstrap with resampling and replacement. A simulation-based diagnostic was performed by visual predictive checks.

Several combinations of absorption and distribution models were assessed: zero-order, first-order, mixed zero- and first-order (simultaneous and sequential), with or without lag time, and transit compartments. Multiple-fraction absorption kinetics and a shunt model were evaluated to describe the second absorption peak. Distribution models tested included open 1-, 2-, and 3-compartment, and nonlinear tissue distribution from central and/or peripheral compartment. Model reductions were investigated by traditional model-fitting criteria. BSV was modelled as lognormal and was tested on all model parameters, followed by stepwise elimination when their estimation was not adequately supported by the data. Additive, proportional, and mixed error models were tested to describe unexplained residual variability.

A Bayesian approach conditioned on the population characteristics was used to estimate the individual PK model parameters, which were fixed and used as an input function to the PD model. Raw LPS-induced TNFα secretion data of both 3-[5-amino-4-(3-cyanobenzoyl)-pyrazol-1-yl]-N-cyclopropyl-4-methylbenzamide and placebo-treated subjects was modelled simultaneously. Direct and indirect response models, with or without negative feedback, were explored. The final description of the PD data was an indirect response model with negative feedback on the system's outflow rate and non-stationarity in production of response (Eqs. 1-3).

The following expression was used to describe the oscillatory behavior of the baseline:

$$K_{in,circ} = K_{in} + A \cdot K_{in} \cdot \cos[\omega \cdot (t-t_0)] \quad (1)$$

where t is time, Kin is the average input rate, and t0 the shifted peak in response. The x parameter scales the frequency of oscillations to the physical frequency 2p/cycle, where cycle equals 24 hours. Parameter A is the fraction of Kin that corresponds to the amplitude. The differential equation for ex vivo LPS-induced TNFα secretion (E) employed Eq. 2:

$$dE/dt = K_{in,circ} \cdot (1-(C1 \cdot I_{max})/(IC_{50}+C1)) - K_{out} \cdot E \cdot M \quad (2)$$

where Kout is the first-order degradation rate constant, C1 the central drug concentration, Imax the maximum inhibition, and IC50 the drug concentration at half maximum inhibition. Eq. 2 was initialized as $E(0)5K_{in,circ}/K_{out}$. E is counterbalanced by the ability of molecular mechanisms, denoted by M, that may regulate cellular adaptation processes to control the magnitude and duration of LPS-induced p38 activation. Production of M is governed by relative E to baseline (E/E0) and the first-order rate constant ktol (Eq. 3).

$$dM/dt = ktol \cdot (E/E0) - ktol \cdot M \quad (3)$$

In the absence of any drug, relative drug response (E/E0) and M are unity at baseline. In response to drug effect, the first-order decline of M is governed by ktol.

le;2qThe patents and publications listed herein describe the general skill in the art and are hereby incorporated by reference in their entireties for all purposes and to the same extent as if each was specifically and individually indicated to be incorporated by reference. In the case of any conflict between a cited reference and this specification, the specification shall control. In describing embodiments of the present application, specific terminology is employed for the sake of clarity. However, the invention is not intended to be limited to the specific terminology so selected. Nothing in this specification should be considered as limiting the scope of the present invention. All examples presented are representative and non-limiting. The above-described embodiments may be modified or varied, without departing from the invention, as appreciated by those skilled in the art in light of the above teachings. It is therefore to be understood that, within the scope of the claims and their equivalents, the invention may be practiced otherwise than as specifically described.

TABLE 1

Stochastic simulation (N = 500) of drug response (inhibition of LPS-induced TNFα secretion) in relation to dosing schedule

| PD parameter | Total cumulative dose of 75 mg Single treatment period of 14 days 25 mg day 1, 6, and, 10 | Total cumulative dose: 225 mg/cycle one cycle = 6 weeks[a] 75 mg on day 1, 6, and 10 of each cycle |
|---|---|---|
| $I_{max}$ (%) | 57.7 [49.3; 64.2] | 65.0 [58.6; 68.3] |
| $T_{min}$ (h) | 27 [26; 28] | 27 [26; 28] |
| Time above 50% inhibition from baseline in 14-day treatment period or cycle (h) | 36 [0; 96] | 125 [44.1; 177] |
| Average % inhibition from baseline over 14-day treatment period or cycle | 32.9 [23.5; 41.0] | 15.1 [15.1; 20.3] |
| Average % inhibition from baseline in first 2 days | 44.3 [35.9; 51.9] | — |

TABLE 1-continued

Stochastic simulation (N = 500) of drug response (inhibition of
LPS-induced TNFα secretion) in relation to dosing schedule

| PD parameter | Total cumulative dose of 75 mg Single treatment period of 14 days 25 mg day 1, 6, and, 10 | Total cumulative dose: 225 mg/cycle one cycle = 6 weeks[a] 75 mg on day 1, 6, and 10 of each cycle |
|---|---|---|
| Average % inhibition from baseline in first 3 weeks of the cycle | — | 30.1 [21.3; 40.6] |

Data are median [5th percentile, 95th percentile] of 500 simulations using model parameters of Table 1.
$I_{max}$, maximum inhibition from baseline; $T_{min}$, time to inhibition nadir.
[a] PD data of cycle 2 (steady-state).

What is claimed is:

1. A method for the treatment of acute exacerbations of an inflammatory respiratory disease in a human patient suffering from an inflammatory respiratory disease where the acute exacerbation is affecting the respiratory tract, comprising administering to a human patient in need thereof three to five separate therapeutically effective doses of 3-[5-amino-4-(3-cyanobenzoyl)-pyrazol-1-yl]-N-cyclopropyl-4-methylbenzamide or a pharmaceutically acceptable salt, hydrate, or solvate thereof over a minimum period of five days and a maximum period of ten days, with at least one day between every dose.

2. A method of alleviating a symptom of an acute exacerbation of an inflammatory respiratory disease in a human patient suffering from an inflammatory respiratory disease where the acute exacerbation is affecting the respiratory tract, comprising administering to a human patient in need thereof three to five separate therapeutically effective doses of 3-[5-amino-4-(3-cyanobenzoyl)-pyrazol-1-yl]-N-cyclopropyl-4-methylbenzamide or a pharmaceutically acceptable salt, hydrate, or solvate thereof over a minimum period of five days and a maximum period of ten days, with at least one day between every dose.

3. A method of increasing the tolerability of 3-[5-amino-4-(3-cyanobenzoyl)-pyrazol-1-yl]-N-cyclopropyl-4-methylbenzamide or a pharmaceutically acceptable salt, hydrate, or solvate thereof in a human patient suffering from an inflammatory respiratory disease, which comprises administering to a human patient in need thereof, and where said patient is suffering an acute exacerbation affecting the respiratory tract, three to five separate doses of a pharmaceutical composition comprising 3-[5-amino-4-(3-cyanobenzoyl)-pyrazol-1-yl]-N-cyclopropyl-4-methylbenzamide or a pharmaceutically acceptable salt, hydrate, or solvate thereof, over a minimum period of five days and a maximum period of ten days, with at least one day between every dose administration.

4. The method of claim 1, wherein three separate doses are given over a minimum period of five days and a maximum period of seven days, with at least one day between every dose administration.

5. The method of claim 1, wherein four separate doses are given over a minimum period of seven days and a maximum period of ten days, with at least one day between every dose administration.

6. The method of claim 1, wherein five separate doses are given over a period ten days, with at least one day between every dose administration.

7. The method of claim 1, wherein said inflammatory respiratory disease is selected from the group consisting of asthma, COPD, cystic fibrosis, and adult respiratory distress syndrome.

8. The method of claim 7, wherein the acute exacerbation of an inflammatory respiratory disease is an acute exacerbation of asthma.

9. The method of claim 1, wherein the amount of the dose of 3-[5-amino-4-(3-cyanobenzoyl)-pyrazol-1-yl]-N-cyclopropyl-4-methylbenzamide or a pharmaceutically acceptable salt, hydrate, or solvate thereof is reduced over the course of at least the first three separate administrations.

10. The method of claim 1, wherein the initial dose of 3-[5-amino-4-(3-cyanobenzoyl)-pyrazol-1-yl]-N-cyclopropyl-4-methylbenzamide or a pharmaceutically acceptable salt, hydrate, or solvate thereof is at least 20% greater than any of the subsequent doses.

11. The method of claim 9, wherein the third dose is a smaller dose than the second dose.

12. The method of claim 1, wherein the dose is administered on days 1, 6 and 10, and the dose is 25 mg or 75 mg.

13. The method of claim 1, wherein said patient is administered no more than three separate therapeutically effective doses of 3-[5-amino-4-(3-cyanobenzoyl)-pyrazol-1-yl]-N-cyclopropyl-4-methylbenzamide, wherein the effective dose is 75 mg, and wherein the doses are administered on days 1, 6 and 10.

14. The method of claim 1 wherein said patient is administered not more than three separate therapeutically effective doses of 3-[5-amino-4-(3-cyanobenzoyl)-pyrazol-1-yl]-N-cyclopropyl-4-methylbenzamide, wherein the effective dose is 25 mg, and wherein the doses are administered on days 1, 6 and 10.

15. The method of claim 13, wherein the acute exacerbation of an inflammatory respiratory disease is an acute exacerbation of asthma.

16. The method of claim 14, wherein the acute exacerbation of an inflammatory respiratory disease is an acute exacerbation of asthma.

* * * * *